(12) United States Patent
Husted et al.

(10) Patent No.: US 7,464,715 B1
(45) Date of Patent: *Dec. 16, 2008

(54) DENTAL CLEANING DEVICE

(75) Inventors: Eston A. Husted, St. Paul, MN (US); Mardelle M. LaMoure, 1750 S. Mississippi River Blvd., St. Paul, MN (US) 55116

(73) Assignee: Mardelle M. LaMoure, Saint Paul, MN (US)

( * ) Notice: Subject to any disclaimer, the term of this patent is extended or adjusted under 35 U.S.C. 154(b) by 57 days.

This patent is subject to a terminal disclaimer.

(21) Appl. No.: 11/042,374

(22) Filed: Jan. 25, 2005

Related U.S. Application Data

(63) Continuation-in-part of application No. 10/458,587, filed on Jun. 10, 2003, now Pat. No. 7,055,530.

(60) Provisional application No. 60/558,756, filed on Apr. 1, 2004.

(51) Int. Cl.
*A61C 15/00* (2006.01)

(52) U.S. Cl. .................................................. 132/321
(58) Field of Classification Search .............. 132/321, 132/323–325, 329; 15/244.1
See application file for complete search history.

(56) References Cited

U.S. PATENT DOCUMENTS

| | | | | | |
|---|---|---|---|---|---|
| 3,511,249 | A | * | 5/1970 | Baitz | 132/329 |
| 4,270,556 | A | * | 6/1981 | McAllister | 132/321 |
| 4,450,849 | A | * | 5/1984 | Cerceo et al. | 132/321 |
| 5,967,154 | A | * | 10/1999 | Anderson | 132/321 |
| 6,003,525 | A | * | 12/1999 | Katz | 132/321 |
| 7,055,530 | B2 | * | 6/2006 | Husted | 132/321 |

* cited by examiner

*Primary Examiner*—Robyn Doan
(74) *Attorney, Agent, or Firm*—Anthony G. Eggink; Katrina M. Eggink

(57) ABSTRACT

A dental cleaning strip constructed of a polymeric material having a plurality of spaced openings having raised peripheral portions for cleaning interproximal surfaces and contact areas between teeth. The polymeric material may be formed into apertured strips by means of a laser. The raised peripheral portions of the flexible strips may have raised irregular peripheral shapes extending from at least one surface thereof.

19 Claims, 6 Drawing Sheets

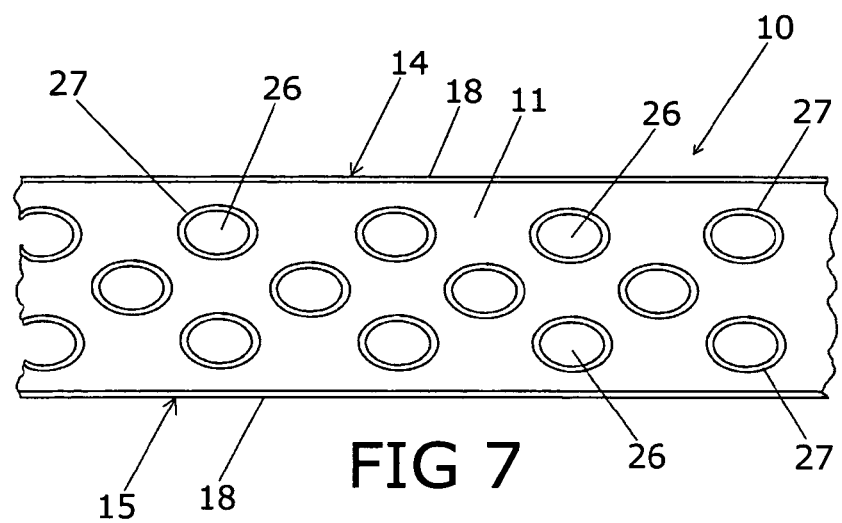
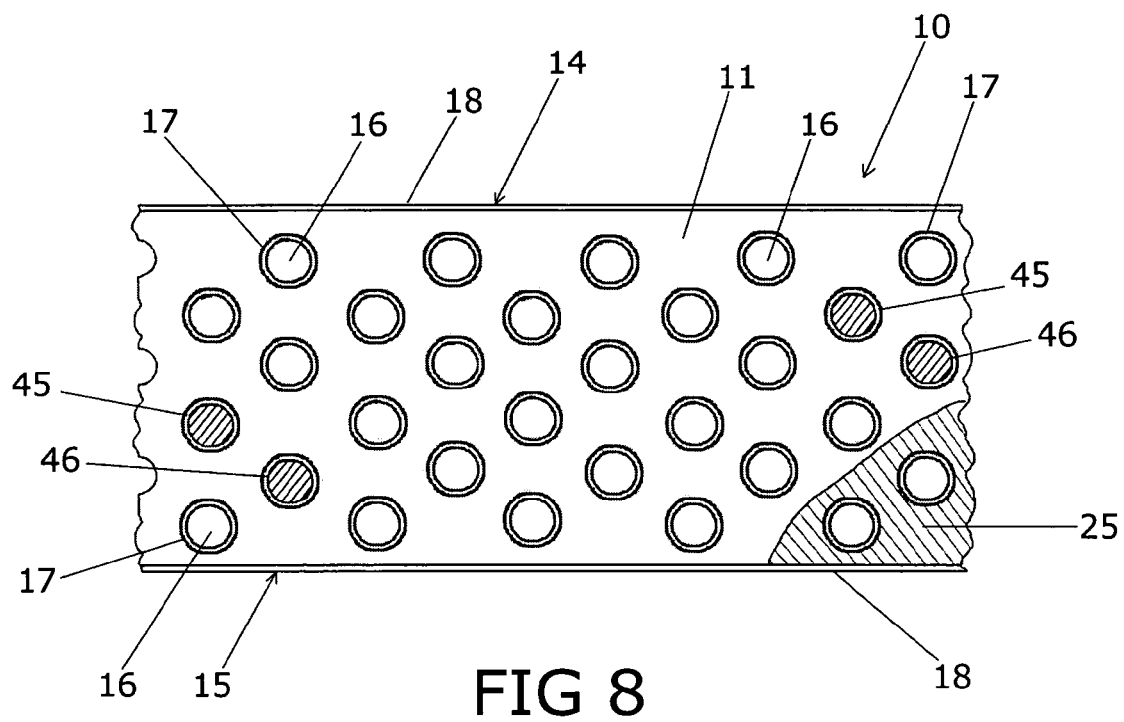

DENTAL CLEANING DEVICE

This application is a Continuation-in-Part of pending U.S. patent application Ser. No. 10/458,587, filed on Jun. 10, 2003 now U.S. Pat. No. 7,055,530 and claims the benefit of Provisional Patent Application Ser. No. 60/558,756, filed on Apr. 1, 2004.

BACKGROUND OF THE INVENTION

The present invention relates generally to devices for cleaning teeth and a process for making such teeth cleaning devices. Particularly, this invention relates to flexible and rigid polymeric dental cleaning strip devices usable by consumers to clean the interproximal areas between the teeth as well as at and below the gum line.

The importance of oral hygiene is well documented. Gum disease, essentially being a chronic infection causing inflammation, has been linked to major degenerative diseases; see "The Secret Killer", *Time* Magazine, Feb. 23, 2004. As stated in the article, the importance of preventing gum disease is imperative, particularly in view of the link found between chronic inflammation and heart disease, cancer, Alzheimer's and other diseases. Subsequently, two studies reported in the Jan. 6, 2005 issue of *New England Journal of Medicine* showed a link between chronic inflammation from conditions like periodontal disease and increased levels of CRP or C-reaction protein which was found to be a key factor in heart disease.

Various devices and techniques are presently used by individuals for teeth cleaning and oral hygiene purposes. An individual may typically use a tooth brush with toothpaste which may contain abrasive materials, to clean the exterior surfaces of the teeth. For cleaning the interproximal or areas between the teeth, dental floss has usually been utilized. Dental floss which is marketed in many forms and configurations, i.e., from round floss to dental tape, may comprise string or other material such as cotton or like materials of a specified diameter or thickness. Dental floss and dental tape are manipulated between the teeth to aid in cleaning and removing debris from between the teeth and at the gum line. Dental floss, particularly when formed of cotton, however, is usually too soft to effectively remove tartar, calcified plaque and other stain material from tooth surfaces. Dentists and dental hygienists are consulted to remove the latter using various scaling tools and other methods. The consumer, therefore, is limited to the tools, i.e., tooth brushes and cotton floss, and techniques available in the marketplace for cleaning teeth.

The dental cleaning devices of the present invention are designed for consumer use and include generally elongated polymeric compositions having ridged apertures which permit the cleaning devices to be used between the teeth and against the gum line. The dental cleaning devices, i.e., cleaning strips, permit the consumer to clean teeth to a degree beyond the results obtained from using presently known devices designed for consumer use. The flexible and semi-rigid apertured polymeric devices may be provided in various cooperating assemblies and overcome the limitations of prior art teeth cleaning structures. The term dental strip used herein is used broadly and includes the terms tape and floss, and includes dental strips having generally flat, round, oval and other geometric cross-sectional configurations.

It is an advantage of the present invention to provide a flexible polymeric cleaning member or strip, i.e., constructed of an elongated nylon or polytetrafluoroethylene (PTFE) material or the like, having, for example, a plurality of volcanic-like apertures extending from a surface of the elongated material. The dental cleaning strips may be inserted between the teeth and used in a manner similar to known dental floss. The dental cleaning strips of the invention may be provided in a variety of structures and configurations, each being constructed and arranged to provide the consumer with an easy and effective means to clean and care for teeth. The dental cleaning strips may also be provided with coatings and agents which may be released for transfer during teeth cleaning procedures.

SUMMARY OF THE INVENTION

This invention comprises dental cleaning devices to promote good oral hygiene and which include various polymeric structures as well as holders for the polymeric dental cleaning structures. The dental cleaning devices may comprise elongated flexible polymeric member, strips or tape having a plurality of apertures with raised edges or peripheries for engaging and cleaning the teeth of a user. The elongated member, strip, ribbon, floss or tape may have various cross-sectional configurations, i.e., rectangular, circular, etc. and formed of a polymeric material which may be uniform, fibrous or woven in structure. Raised edges or peripheries may be formed around each aperture and extend outwardly on at least one surface of the strip so that the strip cleans the interproximal areas of the teeth and gum line when manipulated during use. The raised edges about the apertures may also be formed of materials such as releasable agents and compositions. When formed of generally flat cleaning strips, the edges of the strips may also have raised peripheral edge portions. Specific embodiments are provided for interproximal teeth cleaning only, and other embodiments are provided for use at and below the gum line tissue.

The dental cleaning strip is preferably constructed of a flexible polymeric material, such as nylon, PTFE or the like and which is softer than tooth enamel. Tooth enamel hardness has been found to be approximately Brinell 350. The flexible polymeric material of the present invention has a hardness less than the hardness of tooth enamel. However, the hardness of the polymeric material may be controlled and may exceed the cleaning action of typical cotton or waxed cotton dental floss.

The present invention further relates to a polymeric dental cleaning member or strip which may be shaped or configured utilizing a melting process. The melting process, for example, may utilize a laser process wherein individual laser beams are directed at a length of polymeric material or a moving polymeric web (a moving length of polymeric roll stock material, i.e., nylon, PTFE or the like) which shape the strip, the strip edges and the location, shape and the peripheral structural outline of the holes, lines or aperture pattern of the polymeric strip material. Alternatively, the elongated material may comprise a PTFE material wherein a laser is used to impart apertures with raised edges on one or both surfaces thereof. The ridged apertures may also be provided subsequent to strip formation or subsequent to the placement of a strip portion in a holder device, i.e., in a single use flosser device. The melting process may be controlled by the physical and thermal properties of the selected polymer, such as thickness, melting point as well as the type of laser and laser beam controls of the laser beam assembly. Laser beams may be directed or reflected to impart energy to any portion at any angle of the strip, either moving or at rest. For example, volcanic apertures may be imparted through the cleaning strip so as to provide alternating volcanic apertures on both sides of the strip. Although the use of lasers are discussed herein, other melting or molding means and processes, including physical means to impart apertures in a substrate, may be utilized to practice the processes and making the cleaning strip devices of this invention.

The dental cleaning members or strips of the invention may be colored, printed, coated and shaped to provide various dental cleaning benefits. The coatings and/or agents may also be utilized to create peripheral ridges about the apertures and dental strip side edges. For example, the strips may be colored, i.e., blue or be printed for identifying a specific product type directed to specified uses, i.e., consumer type, thickness and cleaning ability. Coatings and/or agents may be provided on the strip surfaces or captured in the apertures for medical and dental benefits. The dental strips may also have widened or thickened strip handle portions for ease of dental strip use.

In addition to surface coatings, materials or agents may be imbedded or captured within individual apertures so as to be dispersed or released onto the interproximal areas automatically as the user causes the apertures to pass between the teeth. The transferred materials may be dissolvable by saliva, for example.

The coatings and release agents used in connection with the dental cleaning strips of the invention provide a "put and take" effect whereby cleaning agents and the like are placed onto and between the teeth while debris and plaque are taken away via the ridged apertures and/or side edges of the cleaning strip device.

The dental cleaning devices of the invention may be provided in roll or strip form, and may have different cleaning properties on the opposing strip surfaces. A laser process may be utilized to control the various physical properties of the cleaning strip.

The dental cleaning members may also be provided or incorporated into a holder device or assembly, i.e., a single use flosser, whereby a short length or predetermined area of polymeric material with apertures having peripheral ridges is provided for the controlled manipulation between the teeth. The holder device may utilize a strip having a generally flat or rectangular cross-sectional configuration or a strip having a generally round cross-sectional configuration. The holder device may have a structure and configuration which secures and cooperates with the cleaning strip to control the depth of use of the cleaning strip with respect to the gum line, if so desired.

These and other benefits of this invention will become apparent from the following description by reference to the drawings.

BRIEF DESCRIPTION OF THE DRAWINGS

FIG. 7 is a top plan view showing another embodiment of the invention;

FIG. 8 is a top plan view showing another embodiment of the invention;

DESCRIPTION OF THE PREFERRED EMBODIMENTS

Figure 1:
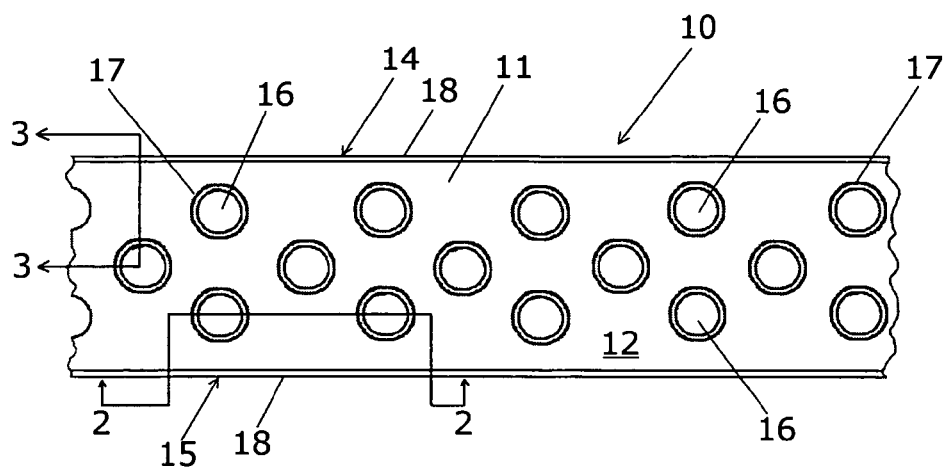
FIG. 1 is a top plan view of a length of the dental cleaning strip of the present invention.
Figure 2:
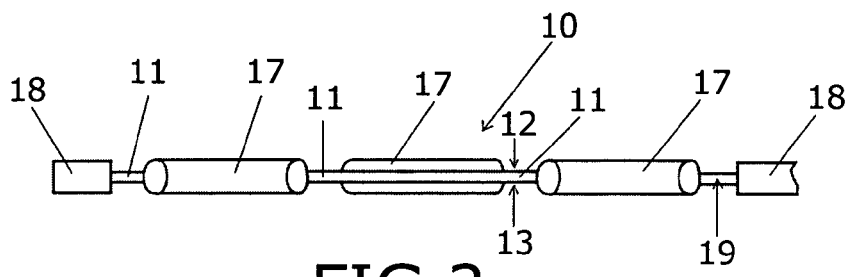
FIG. 2 is a sectional view of the dental cleaning strip taken along lines 2-2 of FIG. 1.
Figure 3:
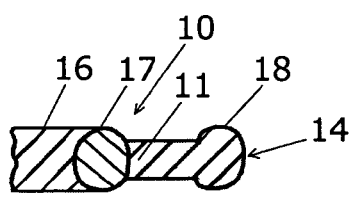
FIG. 3 is a sectional view of the dental cleaning strip taken along lines 3-3 of FIG. 1.

Referring to FIGS. 1-3, the dental strip 10 of the invention is shown comprised of an elongated strip body 11 having opposing surfaces 12 and 13. The strip body 11 is flexible, has side edges 14 and 15 and a pattern of holes or apertures 16. The side edges 14 and 15 are shown to have raised edges 18 and each aperture 16 has a raised ridge 17 thereabout. The strip body 11 has a thickness 19 and the raised edges 18 as well as the raised ridges 17 defining each aperture 16 extend upward and downward whereby both opposing surfaces 12 and 13 have predetermined elevated or raised areas.

The strip body 11 of the invention is preferably constructed of a polymeric material which is strong and flexible so that it may be manipulated between the teeth of a user. For example, nylon and PTFE have been found suitable, although any flexible polymeric or like material may be used within the purview of the present invention. Other flexible polymeric materials and laminations may be used to create the dental cleaning strips, i.e., polyesters, polypropylene, polyethylene and plastic materials used in the medical and packaging fields, and the like. Although the strip body 11 is shown to be generally planar in cross-section, other strip configurations, i.e., generally circular in section, may also be utilized within the purview of the invention.

Figure 4:
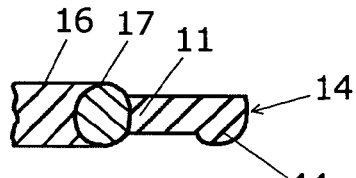
FIG. 4 is a sectional view of another embodiment of the dental cleaning strip of the invention.

FIG. 3 is a sectional view showing the raised edge 18 and the peripheral ridge 17 about the aperture 16 with respect to the relative thickness of the strip body 11. FIG. 4 is another embodiment of edge 14 wherein the thickened or raised edge portion 44 is shown to extend from one surface of strip body 11. It is within the purview of this invention to provide dental cleaning strips having raised edges 18 and/or peripheral ridges 17 which extend from one or both sides of the strip body 11. Thus, the strip body may have only raised edges 18, only peripheral ridges 17 or both and having the edges 18 and ridges 17 either extending from one or both sides of the strip body 11, or with any combination thereof.

Figure 5:
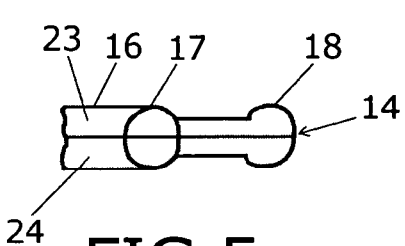
FIG. 5 is a sectional view of another embodiment of the dental cleaning strip of the invention.
Figure 6:
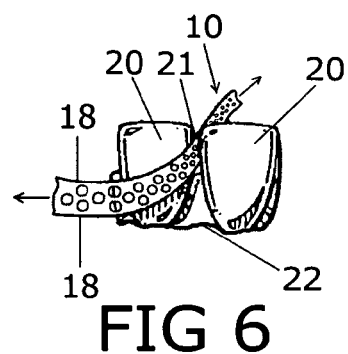
FIG. 6 is a frontal plan view showing the dental cleaning strip used on the teeth of a user.

FIG. 5 shows that the strip body may be constructed of two or more laminated materials, i.e., polymeric layers 23 and 24. As will be further discussed below the different plastic materials 23 and 24 may have different properties, i.e., melting points and hardness, whereby the effect of the dental strip formed of such materials may exhibit or provide different teeth cleaning results. Various additives may also be provided in the polymer, i.e., metallic compounds, to thereby control the thickness and hardness of the cleaning edges and aperture peripheries. FIG. 6 shows the dental strip 10 used in a manner similar to the use of known cotton floss between teeth 20, to clean the interproximal surface 21 and whereby the dental strip 10 is moved in a back and forth motion. Further, because of the raised edges 18 of the dental cleaning strip 10, the strip of this invention may be utilized adjacent to the gum line 22. As will be further discussed, certain dental cleaning strip configurations may be suited for cleaning interproximal teeth areas whereas others may also be suited for cleaning teeth areas adjacent to and below the gum line.

The polymeric dental cleaning strip material 11 may be a flexible film made of nylon 6,6, for example Dartek® C-917 a DuPont nylon film sold by Enhance Packaging Technologies, Inc., for example. This nylon film may be thermoformed, printed, laminated or coated. The film may be provided in thickness of 0.60, 0.75, 1.00, 1.25, 1.50, 2.00, 2.50, 3.00, 4.00 mils, has a melting point of 510° F., has a smooth, uniform surface, has toughness, thin gauge and clarity. These films may be provided in other thicknesses and are typically provided in roll form, however, specified lengths of polymeric materials may also be utilized to form the dental cleaning strips of this invention. For example, polytetrafluoroethylene (PTFE) has also been found suitable for use as a dental cleaning strip according to the teachings of the present invention.

Referring to FIGS. 1 and 7, the dental cleaning strip 10 may utilize differently sized and shaped apertures. For example, FIG. 7 shows a pattern of oval shaped apertures 26, each having a peripheral ridge 27. Although the aperture patterns shown in FIGS. 1 and 7 are each comprised of three rows of apertures, other patterns, whether regular and repeating or irregular and non-repeating may be utilized within the purview of this invention.

Referring to FIG. 8, the dental cleaning strip 10 is shown to be wider than the strips shown in FIGS. 1 and 7. Although the thickness 19 of the strip body may be varied, a wider strip as shown in FIG. 8, may be utilized to permit a user to fold over the strip body 11 to thereby increase the overall thickness and to clean teeth having larger gaps therebetween. As shown, a coating 25 is shown applied to the surface of the strip body 11. Further, materials or agents 45 and 46 are shown captured in several apertures 16 within the confines of peripheral ridges 17. For example, anti-bacterial agents to reduce inflammation, prevent tooth decay, teeth whitening agents, anti-frictional additives, bees wax, toothpaste gel or other coatings and/or agents may be applied to the surfaces of strip 10 or placed or captured within the aperture(s) of the strip. These coatings or agents are provided for use with transport and/or transfer to the teeth of the user. The coatings or agents may be activated when used, for example by dissolving due to saliva. Further, specified widths of the cleaning strips may be provided to veterinarians to clean the teeth of animals.

Figure 9:
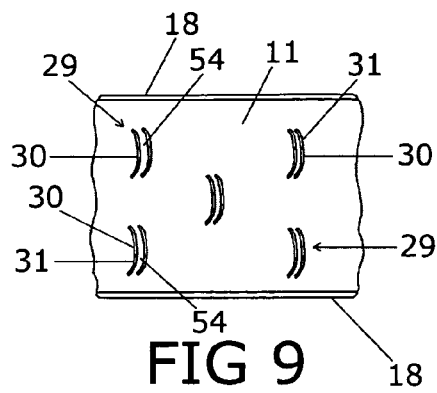
FIG. 9 is a top plan view showing another embodiment of the invention.

Referring to FIGS. 9-12, various aperture shapes and configurations are shown and which may be utilized in the dental cleaning strips of the present invention. Specifically, FIG. 9 shows a crescent slit pattern 29, each comprised of a pair of crescent slit apertures 30. Each slit aperture 30 is shown to have a raised peripheral ridge 31. As shown, the flap portion 54 created by and between the pair of slits 30 provides a flexible segment, unitary at both ends with the strip body 11, which engage the teeth of a user as the dental cleaning strip is moved between the teeth.

Figure 10:
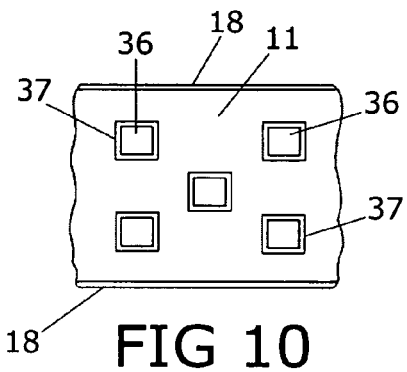
FIG. 10 is a top plan view showing another embodiment of the invention.
Figure 11:
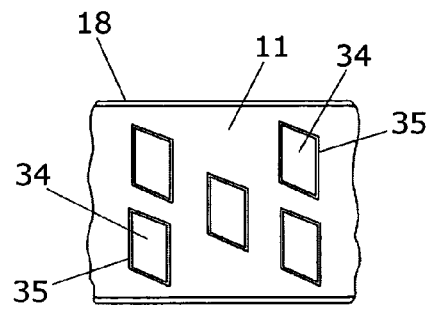
FIG. 11 is a top plan view showing another embodiment of the invention.
Figure 12:
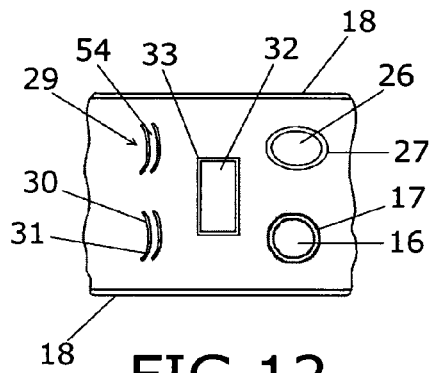
FIG. 12 is a top plan view showing another embodiment of the invention.

FIG. 10 shows a plurality of square apertures 36, each having a square peripheral ridge 37. FIG. 11 shows a plurality of trapezoidal shaped apertures 34, each having a trapezoidal shaped peripheral ridge 35. FIG. 12 shows a dental cleaning strip having a plurality of geometric shapes, namely, crescent slit patterns 29 having slits 30 and ridges 31, a rectangular aperture 32 with a peripheral rectangular ridge 33, an oval aperture 26 with a peripheral oval ridge 27 and a circular aperture 16 having a circular peripheral ridge 17. Each geometric aperture shape may have different teeth cleaning qualities and all may be utilized, alone or in combination, in a cleaning strip according to the present invention.

Figure 13:
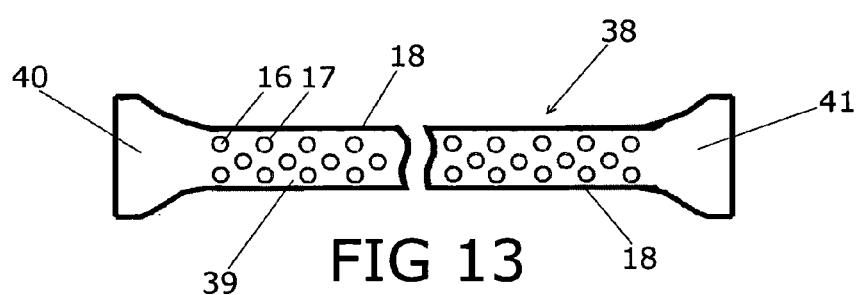
FIG. 13 is a top plan view showing another embodiment of the invention.

Referring to FIG. 13, a dental cleaning strip 38 is shown having an elongated body 39 and opposing handle member 40 and 41. The widened handles 40 and 41 are provided for users having a physical need to be able to grasp a larger strip area, i.e., the elderly, those having arthritis or other physical disabilities. Alternatively, the handle portions may have thickened portions to provide for an easier and more comfortable manipulation grip. The thickened portions may be provided by a dipping process whereby additional material is added to the strip ends. As will be further discussed, the strips of the present invention may be provided in roll form, permitting cut-off lengths as desired by the individual user or in strip form whereby each strip is provided in a predetermined length. The embodiment of FIG. 13 is suitable for the strip length style, i.e., strips of 4-12 inches. As will be further discussed, the cleaning strips of this invention may also be provided in a holder device or assembly wherein the handle of the holder is used to manipulate a cleaning strip or a specified cleaning section held in the operating portion of the holder device.

In use, a length of a dental cleaning strip 10, i.e., 4 inches, is grasped at the ends between thumb and forefinger of each hand to provide a cleaning length of approximately one inch. After slipping the strip between the teeth, a gentle, alternating stroking motion is used to clean the teeth. Thus, the dental cleaning strips may be provided in roll form and cut off to a suitable length by the user and may be provided in predetermined strip lengths. Further, the dental cleaning strips may be provided in various colors which identify or code a specified user group or use type for example, blue—consumer; pink—children (narrower and smaller holes); heavy blue (double normal width) and other colors to identify product thickness.

Figure 14:
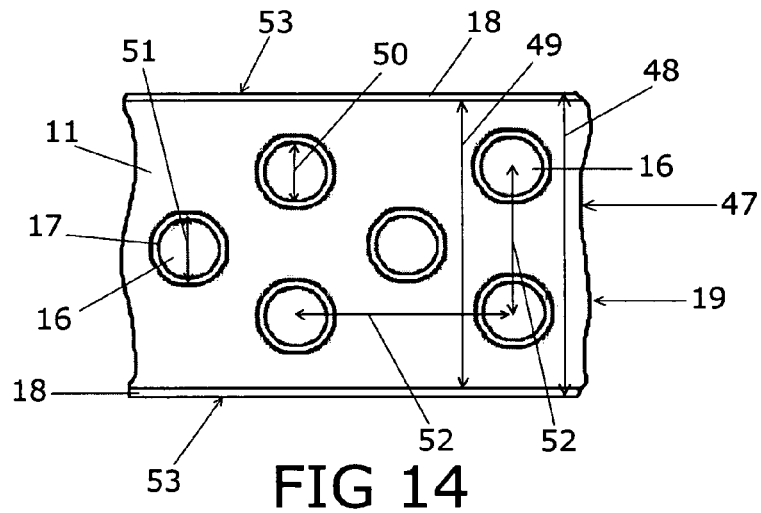
FIG. 14 is a top plan view of a length of the dental cleaning strip of the invention and showing dimensions of various elements thereof.

FIG. 14 shows exemplary dimensions of a dental cleaning strip 10. These dimensions are exemplary only in that the dental strips may be provided having any specified dimensions and characteristics. For example, a dental cleaning strip 10 constructed of nylon film and having a thickness 47 of approximately 0.003 inches has been found suitable for use according to the teachings of the present invention. As shown in FIG. 14 the strip may have an overall width 48 of approximately 0.268 inches and a width 49 of approximately 0.253 inches as measured inside the side ridges 18. The circular apertures 17 are shown to have a diameter 50 of approximately 0.042 inches and the outside diameter 51 of the peripheral ridges 17 being approximately 0.051 inches.

Figure 15:
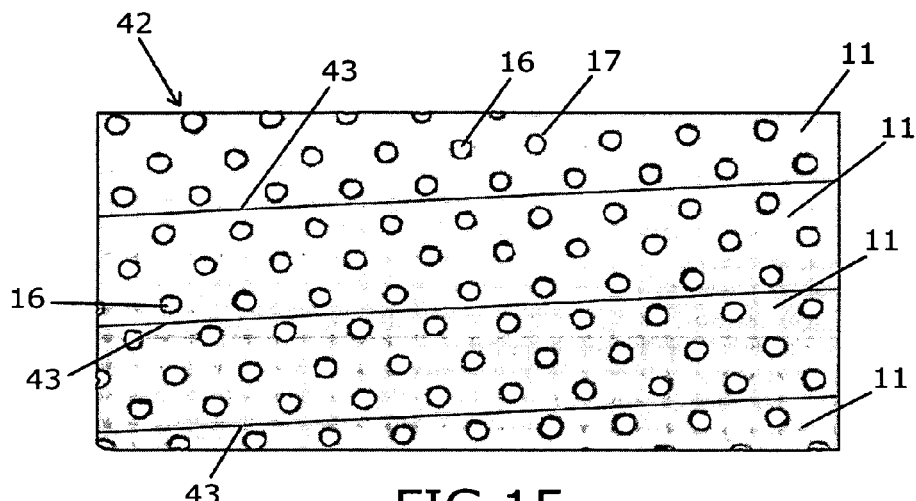
FIG. 15 is a top plan view showing a length of roll stock from which the dental cleaning strip of the invention is made.

Regarding the latter dimension 51, however, this diameter may range from 0.047-0.054 inches. The apertures 16 are shown to be spaced a distance 52 of approximately 0.136 inches, center to center in a generally square pattern, and having one such aperture 16 generally centered in the pattern. The height 53 of the side ridges 18 is shown to be approximately 0.009 inches. When the strips of this invention are produced via a laser process, as shown in FIG. 15, the tolerances may be approximately ±8.0%, for example, with respect to the side ridges, the peripheral edges as well as the aperture diameters. These variations are preferred to provide an irregular cleaning surface. However, dimension tolerances may be controlled to desired specifications.

FIG. 15 shows a photograph of a length of web stock 42 having a plurality of apertures 16. The polymeric material 42 may be provided in roll stock, run through a laser to form the apertures and to slit or cut on lines 43 to form a roll of the dental cleaning strips 10 of the present invention. The laser may also be utilized to provide strips of a specified length.

Figure 16:
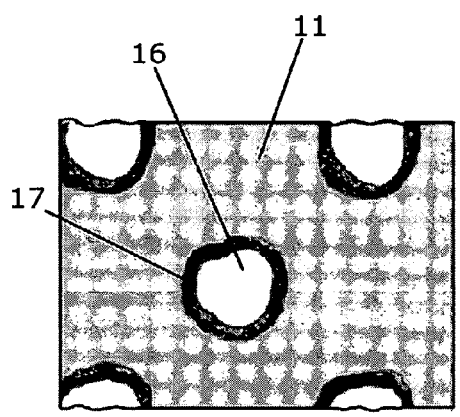
FIG. 16 shows an enlarged area of a portion of the roll stock of FIG. 15.
Figure 17:
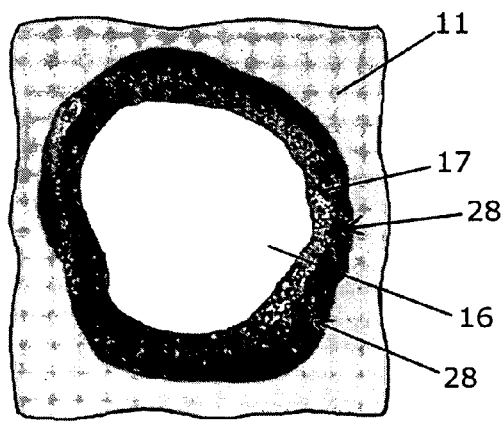
FIG. 17 is a photograph showing an enlarged peripheral ridge formed by the process of the present invention.

FIGS. 16 and 17 show enlarged views of aperture 16 in strip material 11. Particularly, the photograph shows the peripheral ridge 17 defining the aperture 16. This aperture was created via the melting process of a laser operation. Specifically, the irregular shape of the peripheral ridge 17 shows a plurality of volcanic-like, irregular ridge portions 28 which provide the cleaning ridges of the present invention. The irregular ridge portions 28 are a series of alternating sloping surfaces which are the result of the melting and solidifying material which result from the laser process. The irregular ridge portions 28 provide an irregular peripheral cleaning ridge for cleaning and polishing of typically irregular tooth surfaces.

Figure 18:
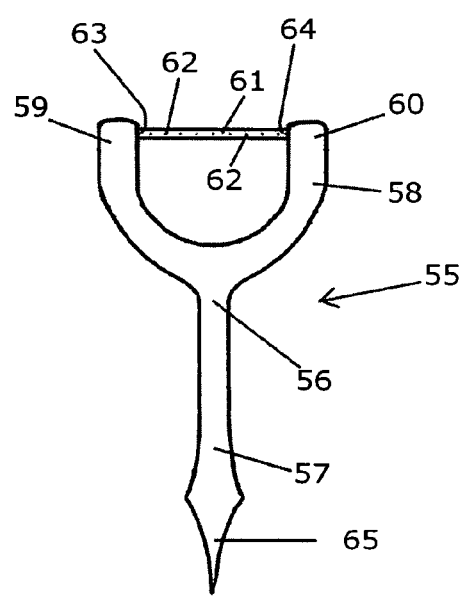
FIG. 18 is a lateral plan view showing a length of the dental cleaning strip incorporated into a holder device.
Figure 19:
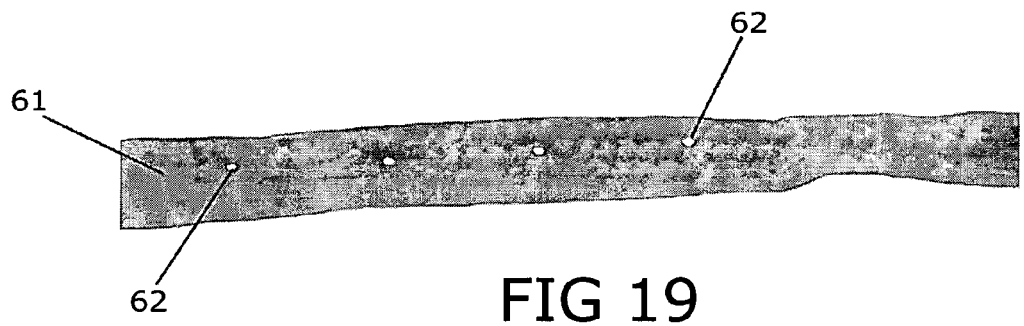
FIG. 19 is a top view showing an elongated fibrous strip having ridged apertures therethrough.
Figure 20:
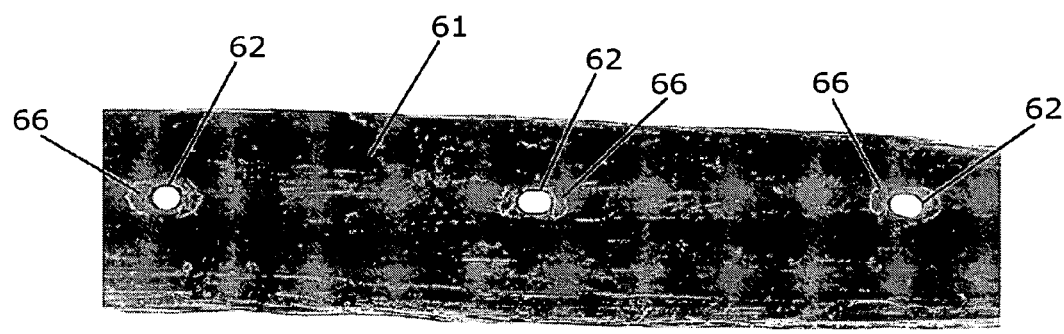
FIG. 20 is an enlarged view of the strip of FIG. 19.
Figure 21:
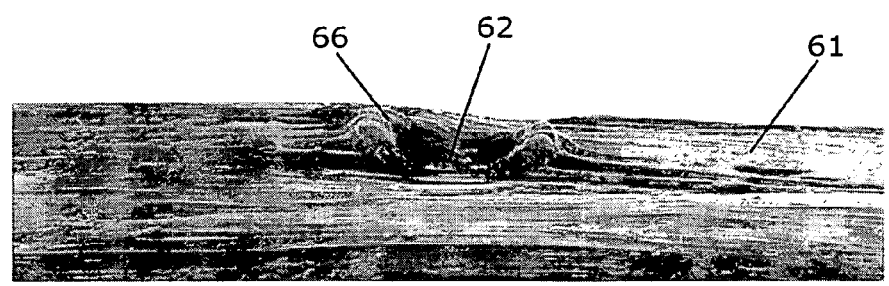
FIG. 21 is an enlarged view of a ridged aperture of the dental cleaning strip of FIGS. 19 and 20.
Figure 22:
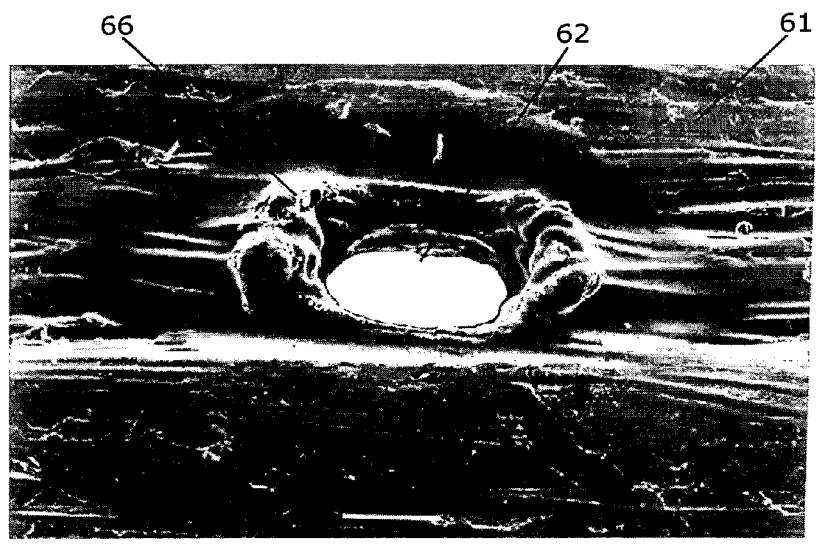
FIG. 22 is a lateral view of the ridged aperture of FIG. 21.

FIG. 18 shows a strip holder device 55 having a holder body 56, a handle portion 57 and an upper portion 58 having opposing leg members 59 and 60. Such holder devices may be known as single use flossers, for example. A length of the dental cleaning strip 61 is shown spanning between the opposing leg members 59 and 60 by means of attachment members 63 and 64. The strip member 61 may have a cross-sectional configuration as previously discussed, i.e., generally round or planar in cross-section and is shown attached to the upper terminal ends of the respective leg members 59 and 60. Attachment may be by encapsulation of the holder body 56, i.e., during formation of the holder body 56 such as during injection molding, for example. Securement may also be provided via other known means. The strip holder device 55 may have any desired structured configuration including known structures which permit the user to manipulate the tension of the cleaning strip during use. In the latter holder configuration a generally round apertured cleaning strip 61 may be used for teeth cleaning including areas at the gum line. The strip member 61 is shown to have a plurality of ridged apertures 62 which are utilized to clean interproximal areas between the teeth. The apertures 62 may be provided in the strip 61 before or subsequent to the positioning of the strip 61 into the holder device 55. Pick point 65 located at the end of handle portion 57 may also be used to clean between the teeth.

FIGS. 19-22 are enlarged views (scanning electron microscope) showing the dental cleaning strip 61 formed of a fibrous polymeric material, having a generally circular cross-sectional configuration. The cleaning strip 61 is shown to have a plurality of apertures 62 therethrough, each having a volcanic-like ridged periphery 66 which extends from the surface of the strip material. The ridged peripheries 66 act to scrape the teeth as the cleaning strip 61 is manipulated between the teeth.

In experimentation using a low power $CO_2$ laser on a PTFE substrate to create holes and volcanic-like ridges and other characteristics for a dental strip, the following dimensions were found representative of a usable dental strip structure: PTFE substrate thickness of 0.0025 inches, inner diameter of hole created—0.0063-0.0065 inches and an overall thickness of ridge and substrate—0.0047 inches; for a PTFE substrate thickness of 0.0043 inches; inner diameter of hole created—0.0051-0.0062 inches and an overall thickness of ridge and substrate 0.0068 inches. The $CO_2$ laser enabled a broad range of settings and adjustments so as to provide the above dimensions, which could also be determined mathematically knowing the chemistry and physics of a given substrate in view of a specific $CO_2$ laser arrangement.

In the process of forming the apertures in the polymeric material which yield the peripheral, volcanic-like ridges about the apertures when a laser beam process, for example, is utilized, differences in the chemical and physical properties are obtained between the base substrate, i.e., PTFE, nylon, etc., and the resultant molten ridges. As shown in the drawings, the reflow is random to thereby form irregular surfaces on the peripheral ridges. During the melting via the laser beam application, the "out-gassing" indicates that the outward flow, cooling and hardening of the remaining material and resultant volcanic-like ridges are the result of a chemically altered structure, i.e., a more concentrated carbon structure, which is relatively harder and exhibits properties clearly different from the base substrate. For example, the coefficient of friction or lubricity is clearly changed in the polymeric material due to the laser beam providing holes in a polymeric substrate. PTFE, for example, is known as a slippery, non-stick material, however, the laser melting process produces irregularly surfaced, molten, volcanic-like ridges which are harder and less slippery, to provide a dental strip having slippery (body strip with lower COF) and non-slippery portions (volcanic ridges with higher COF). The relatively harder and non-slippery ridges permit plaque to be removed from between the teeth of the user, for example. Further, the non-slippery portions permit the adherence of coatings, etc. which would otherwise not adhere to the base substrate. These chemical and physical changes to a laser processed polymeric material are important to the formation of the dental strip materials of the present invention.

Figure 23:
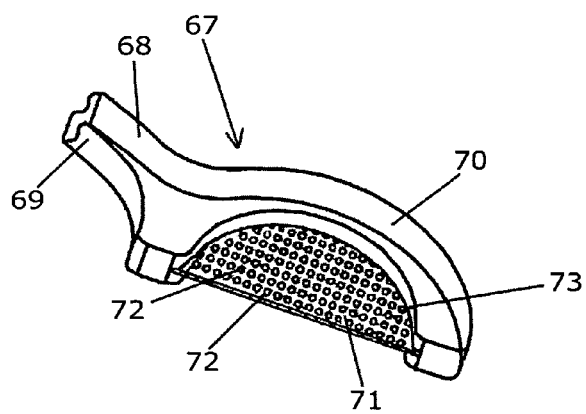
FIG. 23 is a perspective view of another embodiment of the present invention and showing an area of the dental cleaning strip held within a holder structure.
Figure 24:
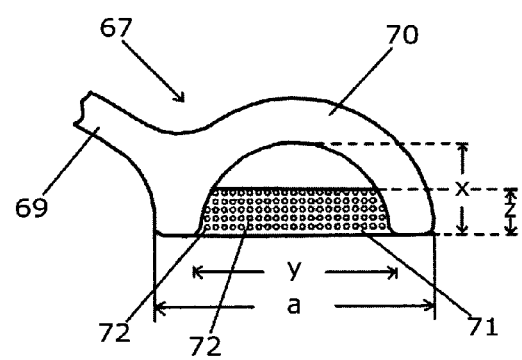
FIG. 24 is a lateral plan view of the embodiment of FIG. 23.
Figure 25:
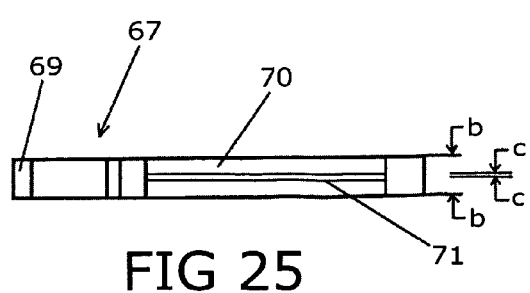
FIG. 25 is a bottom plan view of the embodiment of FIG. 24.

FIGS. 23-25 show an embodiment of a dental cleaning strip holder 67 having a strip holder body 68 with a handle 69 and a terminal strip holding or spanning portion 70 within which is captured a cleaning member area 71 as discussed above. The cleaning strip 71, held in place by attachment 73, is shown to have a plurality of ridged apertures 72. The holder configuration is particularly suited to clean the interproximal areas of the teeth and aids in preventing the cleaning strip edge from engaging the gums of a user. Although the strip portion 71 is shown extending fully within the spanning portion 70, the strip portion may fill only a portion of the spanning area and may yield a configuration similar to the strip 61 configuration shown in FIG. 18. For example, in FIG. 24, the apertured cleaning member 71 is shown having a height "z" and which results in an open area above the cleaning member 71 and the spanning portion 70 of strip holder 67.

FIG. 24 further shows the holder portion having a height "x" which may be the maximum distance that the cleaning strip area of the holder portion is able to be positioned between the teeth of a user. For example, the holder 67 may have a body thickness which prevents the spanning portion 70 from fitting between the teeth of a user and thus providing the maximum distance which the strip area may be utilized between the teeth is "x". The distance "x" may be varied to thereby control the utilization of the strip holder 67 with respect to the gum line. Further, the spanning distance "y"

may also be varied. Thus, although the spanning portion 70 is shown to be hemispherical in configuration, this configuration may be varied. The strip area 71 may be molded into the spanning portion 70 of the holder portion 68 and the ridged apertures 72 may be imparted into the strip area during or subsequent to the molding of the strip holder 67 and the positioning of the strip area therein. The holder may be composed of the same or a different polymeric material as that of the strip area 71. As shown in FIG. 25, the spanning portion 70 may have a thickness "b" of approximately 0.10 inches and the cleaning strip having a thickness "c" of approximately 0.010 inches. The users of these strip holders may be provided with a variety of sizes, each size being coded, i.e., via color for example. Further, enlarged strip holders may be provided for veterinarians for cleaning animal teeth.

Figure 26:
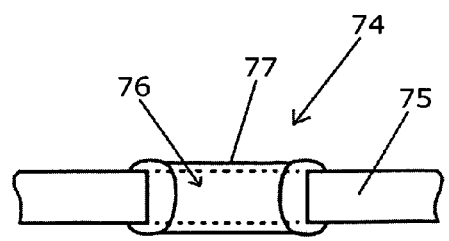
FIG. 26 is a sectional view of another dental cleaning device of the invention.

Referring to FIG. 26, a sectional view of dental cleaning strip embodiment 74 is shown having an elongated body 75 having an aperture 76. The elongated body 75 is polymeric and has an annular ring 77 formed about the periphery of aperture 76. The annular ring 77 may be formed of a different material than the polymeric material comprising the dental strip body 75. Although the peripheral ridges discussed above are referred to as melted polymeric structures caused by a laser process and, therefore, being generally the same material as the base structure, these materials may be different and cooperating. For example, the dental strip body 75 may be PTFE and the annular ring 77 may be formed of an agent such a teeth whitening agent, antibacterial, anti-inflammatory, anti-frictional, toothpaste gel, bees wax compositions and/or other dental or medical related agents. The annular ring 76 may extend about the entire periphery or be a partial peripheral portion about the aperture. The annular ring or grommet like structure may be particularly useful in conjunction with a PTFE base structure in that PTFE (i.e., Teflon) is generally a non-stick material and thus requiring a mechanical-like fastening means. The cleaning or therapeutic materials may be applied to the aperture periphery, positioned within the aperture and/or applied to the cleaning strip edges via a dipping, spraying, roller contact or other means.

When a laser procedure is utilized to form a strip portion, the side or peripheral edge(s) of the strip may have ridges not conducive to gum line contact. Should the treatment of the peripheral edge(s) of any of such ridged strips or the bottom edge of the strip portion in a holder device be treated in such a manner so as to provide a beneficial result to the gum line then the ridged strip itself or the strip portion in the holder device may be configured to allow the edge to engage and clean teeth to and below the gum line.

The cleaning strip area shown in FIGS. 23-25 may have ridged apertures as previously discussed in the application, and particularly as shown in FIGS. 7-12. Thus any pattern of ridged apertures and aperture configurations may be utilized within the purview of the present invention.

As many changes are possible to the dental cleaning strip embodiments and processes of this invention, utilizing the teachings thereof, the description above and the accompanying drawings should be interpreted in the illustrative and not in the limited sense.

That which is claimed is:

1. A unitary dental cleaning strip for cleaning interproximal surfaces and contact areas between teeth, comprising a length of a thin, flexible polymeric material having opposing outer surfaces, a thickness, a hardness and coefficient of friction, said flexible polymeric material having a plurality of spaced openings therethrough and extending along said length of flexible polymeric material, each opening peripherally surrounded by a hardened molten polymeric material having a raised, irregular volcanic-like contoured peripheral ridge protruding from both said opposing outer surfaces of said flexible polymeric material, said hardened polymeric material having an irregular, volcanic-like contoured surface for cleaning purposes, said irregular, volcanic-like contoured surface having a hardness greater than said hardness of said flexible polymeric material and a coefficient of friction higher than said coefficient of friction of said flexible polymeric material, whereby the hardened, less slippery, irregularly shaped volcanic-like contoured peripheral ridges extending from both sides of said strip facilitate the movement of said unitary dental strip and the removal of plaque from interproximal surfaces between teeth.

2. The dental cleaning strip of claim 1, wherein said polymeric material is comprised of a flexible nylon or PTFE and further wherein said polymeric material has a predetermined color.

3. The dental cleaning strip of claim 1, wherein said length of polymeric material has generally parallel side edges and wherein said side edges are raised and have a thickness greater than said thickness of said polymeric material.

4. The dental cleaning strip of claim 3, wherein said raised side edges are thickened portions having irregular surfaces resulting from a laser cutting and polymer melting operation in forming said side edges.

5. The dental cleaning strip of claim 4, wherein said openings are of a geometric shape and arranged in a predetermined pattern and wherein said geometric shape is selected from the group of shapes consisting of a circle, oval, square, rectangle, trapezoid and a crescent shape.

6. The dental cleaning strip of claim 3, wherein said raised side edge thickness and said peripheral ridge of said spaced openings is approximately the thickness of said polymeric material and wherein said raised side edge extends from each opposing surface of said polymeric material.

7. The dental cleaning strip of claim 1, wherein said polymeric material has a coating disposed on one said outer surface and wherein at least one said opening has an agent disposed therein for transfer to the teeth during use.

8. The dental cleaning strip of claim 7, wherein said coating and agent are selected from the group of coatings and agents consisting of teeth whitening, antibacterial, anti-inflammatory, antifrictional, toothpaste gel and bees wax compositions.

9. The dental cleaning strip of claim 1, wherein said polymeric material is comprised of a first layer and a second layer of polymeric material.

10. The dental cleaning strip of claim 1, wherein said polymeric material has a width of approximately 0.250 inches and wherein said openings are generally circular in shape, each having a diameter of approximately 0.040 to 0.050 inches.

11. A dental cleaning strip for cleaning interproximal surfaces and contact areas between teeth, comprising a length of a thin, flexible, polymeric material having opposing outer surfaces, a thickness, a hardness, a coefficient of friction and a plurality of spaced openings therethrough, each opening having a raised, peripheral ridge protruding from both of said opposing outer surfaces, said raised peripheral ridges comprised of a hardened, inflexible material of an irregularly configured surface with a coefficient of friction more than that of said thin flexible polymeric material, and a hardness greater than that of said thin flexible polymeric material, said irregularly configured surfaces further forming a continuous volcanic-like surface on each said protruding peripheral ridge.

12. The dental cleaning strip of claim 11, wherein the polymeric material is nylon or PTFE.

13. The dental cleaning strip of claim 11, wherein said cleaning strip has opposing outer surfaces and further having thickened cleaning and polishing side edges and wherein said polishing ridges and said thickened cleaning and polishing edges are formed by a melting operation and wherein said raised peripheral ridges are approximately the thickness of said flexible material.

14. The dental cleaning strip of claim 11, wherein said apertures are geometric in shape and arranged in a predetermined pattern and wherein said geometric shape is selected from the group of shapes consisting of a circle, oval, square, rectangle, trapezoid and a crescent shape.

15. The dental cleaning strip of claim 11, wherein said polymeric material has a coating disposed on said outer surface.

16. The dental cleaning strip of claim 15, wherein at least one said opening has an agent disposed therein for transfer to the teeth during use.

17. The dental cleaning strip of claim 16, wherein said agent is disposed about the periphery of said opening.

18. The dental cleaning strip of claim 11, further comprising a holder device having a top portion and a handle portion and wherein said dental strip is held in said top portion of said holder device.

19. The dental cleaning strip of claim 11, wherein said raised peripherally disposed annular ridge is comprised of an agent, said agent being selected from the group of agents consisting of teeth whitening, antibacterial, anti-inflammatory, antifrictional, toothpaste gel and bees wax compositions.

* * * * *